United States Patent
Bowald et al.

[11] Patent Number: 5,411,546
[45] Date of Patent: May 2, 1995

[54] DEFIBRILLATION ELECTRODE

[75] Inventors: Staffan Bowald, Almunge; Jakub Hirschberg, Taeby, both of Sweden

[73] Assignee: Siemens Elema AB, Solna, Sweden

[21] Appl. No.: 161,412

[22] Filed: Dec. 6, 1993

[30] Foreign Application Priority Data

Dec. 11, 1992 [SE] Sweden ............... 9203733-2

[51] Int. Cl.⁶ ............................................. A61N 1/05
[52] U.S. Cl. ....................................................... 607/126
[58] Field of Search ............... 607/126, 122, 119, 116, 607/115, 118; 604/104–109

[56] References Cited

U.S. PATENT DOCUMENTS

| | | | |
|---|---|---|---|
| 4,154,247 | 5/1979 | O'Neill | 607/125 |
| 4,414,986 | 11/1983 | Dickhudt et al. | |
| 4,706,671 | 11/1987 | Weinrib | 604/104 |
| 4,825,871 | 5/1989 | Cansell | |
| 4,852,573 | 8/1989 | Kennedy | 607/116 |
| 4,860,769 | 8/1989 | Fogarty et al. | |
| 4,920,979 | 5/1990 | Bullara | |
| 5,016,808 | 5/1991 | Heil, Jr. et al. | 607/122 |
| 5,170,802 | 12/1992 | Mehra | 607/126 |
| 5,221,261 | 6/1993 | Termin et al. | 604/104 |
| 5,235,977 | 8/1993 | Hirschberg et al. | 607/123 |
| 5,256,146 | 10/1993 | Ensminger et al. | 604/104 |
| 5,279,299 | 1/1994 | Imran | 607/126 |

FOREIGN PATENT DOCUMENTS 0373953 6/1990 European Pat. Off. .
WO92/11898 7/1992 WIPO .

*Primary Examiner*—William E. Kamm
*Assistant Examiner*—Kennedy J. Schaetzle
*Attorney, Agent, or Firm*—Hill, Steadman & Simpson

[57] ABSTRACT

A defibrillation electrode, especially for implantation at an intravascular site in a patient, has a flexible electrode cable containing at least one elongate, electrically insulated conductor with an electrode head disposed at a distal end of the electrode cable, and having at least one defibrillation surface for delivering defibrillation pulses to the patient's heart. The electrode head is constructed so as to be radially expandable and, in an expanded position, defines the contours (surface configuration) of a hollow body so as to provide a defibrillation electrode which is affixable to the vessel in which it is sited, and which has a minimal impact on the flow of blood in that blood vessel.

19 Claims, 3 Drawing Sheets

DEFIBRILLATION ELECTRODE

BACKGROUND OF THE INVENTION

1. Field of the Invention

The present invention is directed to a defibrillation electrode of the type for implantation at an intravascular site in a patient.

2. Description of the Prior Art

Defibrillation electrodes are known for implantation at an intravascular site in a patient, these known electrodes generally including a flexible electrode cable containing at least one elongate, electrically insulated conductor with an electrode head, arranged at the distal end of the electrode cable, the electrode head having at least one defibrillation surface for delivering defibrillation pulses to the heart.

One such known defibrillation electrode intended for intravascular implantation is described in European Application 0 373 953. The electrode head of this known defibrillation electrode is a continuation of the electrode cable, and thus the diameter of the electrode head is approximately the same as that of the electrode cable. A disadvantage of this type of defibrillation electrode is that the electrode head cannot be affixed when sited in a blood vessel. Since a defibrillation electrode of this type is always a part of a defibrillation system with a plurality of defibrillation electrodes, longitudinal displacement of the electrode head can result in an undesirable distribution of the current in the heart, since the current distribution is a function of the relative location of all of the electrodes comprising the electrode system. Another disadvantage of this known electrode is that the electrode head is disposed in the bloodstream of the vessel in which it is sited without any lateral control. This can result in an obstruction of the blood flow and also increases the risk of clot formation.

SUMMARY OF THE INVENTION

It is an object of the present invention to provide a defibrillation electrode of the type for intravascular implantation in a patient, which is affixable in the blood vessel in which it is sited with a minimum of disruption of the blood flow within that vessel.

The above object is achieved in a defibrillation electrode constructed in accordance with the principles of the present invention which has a radially expandable electrode head. In the expanded position, the electrode head forms at least the contours (surface configuration) of a hollow body. In an unexpanded position, the electrode head has a diameter which roughly corresponds to the diameter of the electrode cable, and forms a longitudinal continuation of the electrode cable. In this manner, the electrode cable with the electrode head can be introduced without difficulty into a blood vessel. In the expanded position, the diameter of the hollow body formed by the head exceeds the diameter of the blood vessel, so that the hollow body is affixed within the blood vessel by pressing against the surrounding vascular wall after introduction. Because the electrode head is hollow and presses against the vascular wall, the impact on the blood flow in the vessel is minimal.

A patch-type defibrillation electrode is described in U.S. Pat. No. 4,860,769. This electrode head consists of a helical conductor devised such that the electrode head, in profile, is conical. This known defibrillation electrode, however, is intended for implantation in the epicardium, and is therefore not suitable for intravascular use.

Another electrode cable is disclosed in U.S. Pat. No. 4,414,986, which has an electrode ring arranged on the cable for stimulation of the spinal cord of a patient. The electrode cable, designed to press against the dura mater of the spinal cord, has a partially helical preformed shape so as to permit the cable to be affixed at a desired position. The distal end of the electrode cable is provided with an additional affixing means, in the form of outwardly projecting barbs. This type of electrode cable is not suitable for intravascular cardiac use, since the barbs would probably damage the surrounding vascular wall. Moreover, this known cable, as a result of the location and shape of the barbs, would come to lie approximately centrally in a blood vessel, thereby obstructing the flow of blood therein.

In an embodiment of the invention, the body consists of a helical conductor. The advantage of this configuration is that it is highly flexible, and can be implanted even in rather convoluted blood vessels.

In a further embodiment of the invention, the body consists, in part, of the windings of a helical conductor, which are electrically insulated in this area, and a part of a non-helical, substantially straight uninsulated conductor. An electrode head having this constructions provides a conductive surface which can be aimed in a desired direction by rotating the body on its longitudinal axis. In this manner, the electrode can produce an advantageous distribution of current in the heart tissue.

In another embodiment of the invention, the conductor of the electrode cable and the helical conductor form a channel extending the entire length of the defibrillation electrode, and adapted for receiving a stylet. An electrode head or body, with the aid of the stylet, can be straightened, causing the diameter of the body to roughly correspond to the diameter of the electrode cable. This makes the diameter of the body smaller than the inner diameter of the blood vessels in which it is to be introduced, and the blood vessel in which the body is to be sited. When the implanting physician reaches a suitable site in the blood vessel, the stylet can be withdrawn, thereby allowing the electrode to resume its original shape.

In a particularly simple version of the invention, the electrode head can consist of a foil, which in its unexpanded position is helically rolled. An extremely large defibrillation area can then be achieved when the foil is unrolled so that the electrode head assumes its expanded state.

In another embodiment of the invention, the hollow body can have the shape of a cylinder.

In a further embodiment, the cylinder can be formed by parallel, filamentous conductors extending along the longitudinal axis of the cylinder, and interconnected by compressible connector bodies.

In another simple version of the invention, the cylinder can be formed by at least one filamentous conductor having zig-zags along the longitudinal axis of the cylinder. This configuration permits the cylinder to be introduced into blood vessels of varying inner diameters, without any part of the cylinder projecting into the bloodstream and impeding the flow of blood.

In an unexpanded position, the electrode head according to the invention can be inserted into an introductory catheter. This provides another technique for introducing the electrode cable and the electrode head into blood vessels without damaging the surrounding vascular walls.

The electrode head, in a further embodiment, can consist of a shape-memory metal. An electrode head consisting of this material has a specific initial shape, at a first temperature, suitable for implantation of the electrode device in a blood vessel. At a second temperature, for example, at body temperature, the electrode head assumes the shape of a cylinder, or the contours thereof.

In a preferred embodiment of the invention, the entire interior of the body serves as a defibrillation surface. This results in a relatively large defibrillation area, which does not cause damage to surrounding vascular walls when a high amplitude current is delivered, because an appropriate current density is thereby achieved.

In a further embodiment of the invention, the exterior of the body is provided with a defibrillation surface which extends along the longitudinal axis of the body. This is another way of enabling the implanting physician to aim the current field in the desired direction by rotating the electrode head or cylinder on its longitudinal axis.

DESCRIPTION OF THE PREFERRED EMBODIMENTS

Figure 1:
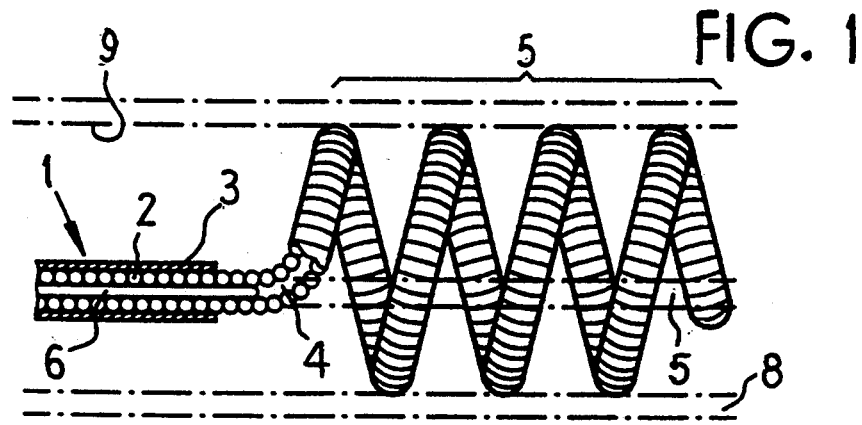
FIGS. 1-8 respectively show different embodiments of an electrode device constructed in accordance with the principles of the present invention, with different versions of electrode heads, in both expanded and unexpanded states.

The distal end of an electrode device constructed in accordance with the principles of the present invention for intravascular placement in a patient is shown in FIG. 1. The electrode device, which is partially shown in longitudinal cross-section, includes an electrode cable 1 consisting of an elongate, helical, flexible conductor 2, having an exterior provided with a layer of insulation 3. A channel 4 is formed in the interior of the wound conductor 2. The electrode device includes an electrode head 5 for defibrillating a heart, disposed at the distal end of the conductor 2. In the embodiment of FIG. 1, the electrode head 5 is an uninsulated continuation of the electrode cable 1, so that the conductor 2 forms a defibrillation surface. The portion of the conductor 2 which constitutes the electrode head 5 is itself arranged in a helical configuration, thereby forming the contours (defining a surface) of a hollow cylinder. As a result of the construction of the electrode device, the channel 4 passes through the entire length of the electrode device, including the electrode head 5. When the electrode device is implanted in a blood vessel 8, a stylet 6 is inserted into the channel 4, thereby straightening the electrode head 5, as indicated by the straightened version of the electrode head 5 shown in dot-dash lines. The diameter of the electrode device thereby becomes smaller than the inner diameter of the blood vessels which it must traverse, and is also smaller than the inner diameter of the blood vessel 8 in which the electrode head 5 is to be sited. When the implanting physician has decided on an appropriate location for the electrode head 5, the stylet can be withdrawn, causing the electrode head 5 to expand in a radial direction, and accordingly permitting the electrode head to resume its preshaped, helical, cylindrical configuration. The electrode head 5 is shaped so that in the expanded position, i.e., when the electrode head assumes the contours of a cylinder, the diameter of the cylinder exceeds the inner diameter of the blood vessel 8 in which it is to be sited, thereby affixing the cylinder formed by the electrode head 5 to the surrounding inner vascular wall 9 with pressure. In the affixed position, the cylinder of the electrode head 5 forms a relatively large defibrillation surface against the vascular wall 9. At the same time, the shape of the cylinder of the electrode head 5 has the advantage of permitting blood to flow substantially unimpeded through the vessel 8, thereby minimizing the risk of clot formation. Additionally, the electrode device permits repositioning of the electrode head 5 in an easy manner, by reinserting the stylet 6 into the channel 4, and again straightening the electrode head 5.

Figure 2:
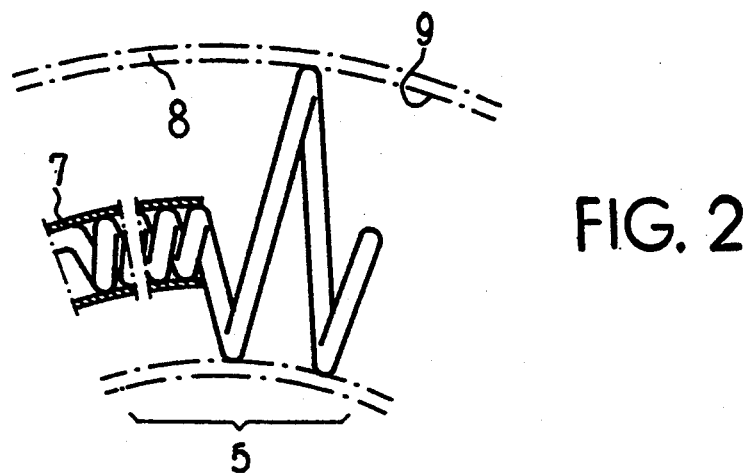

As shown in FIG. 2, the physician can use an introductory catheter 7, instead of a stylet, for implantation of the electrode device of the invention. The electrode cable 1, with the electrode head 5 straightened, is inserted into the introductory catheter 7, the introductory catheter 7 being sufficiently stiff to keep the electrode head 5 straightened, or at least in a configuration having a small diameter in the form of a "mini helix." FIG. 2 shows that the electrode head 5 in the form of a mini-helix can be advanced along the inside of the introductory catheter 7. When the electrode head 5 reaches the desired position, the introductory catheter 7 can be withdrawn, enabling the electrode head 5 to resume its pre-shaped configuration, thereby exerting pressure against the inner wall 9 of the blood vessel 8, as partially shown in FIG. 2.

Figure 3:
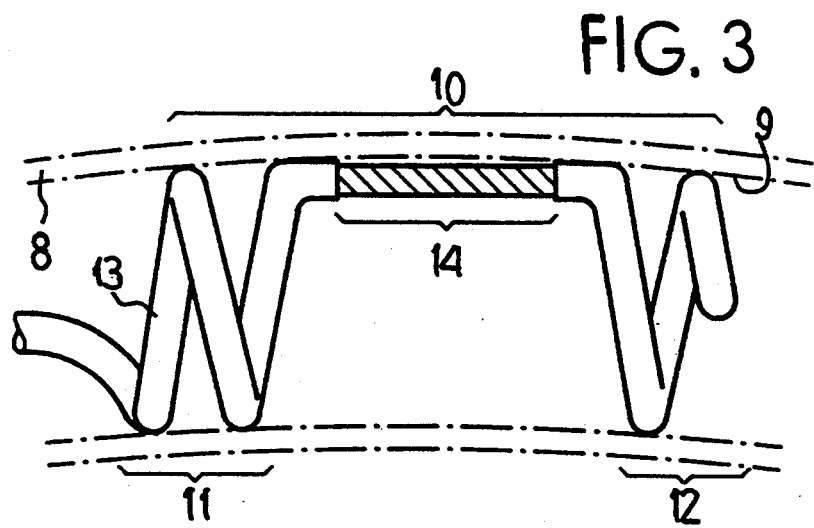

The electrode head 10 in the embodiment of FIG. 3 forms at least the contours of a hollow cylinder. The cylinder formed by the electrode head 5 consists in part of windings 11 and 12 of a helical conductor 13, which is electrically insulated, and also consists in part of a substantially straight, uninsulated conductor length 14, which can be a part of the conductor 13, extending between the windings 11 and 12. The electrode head 10 can be implanted using a stylet, as described in conjunction with FIG. 1, or using an introductory catheter, as described in conjunction with FIG. 2. As a result of this construction of the electrode head 10, the conductor 14 can serve as the defibrillation surface, and thus the field of the defibrillation current can be aimed in a desired direction when the physician rotates the cylinder formed by the conductor head 10 around its longitudinal axis.

Figure 4:
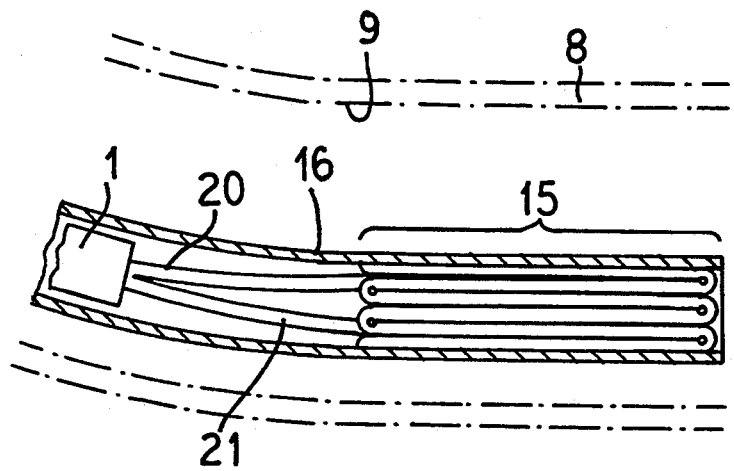
Figure 5:
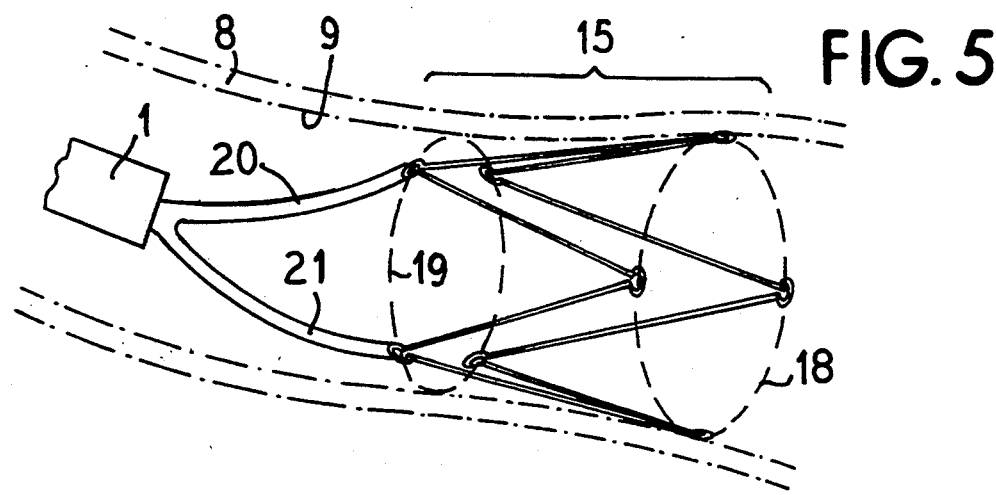

Another example of an electrode head 15 constructed in accordance with the principles of the present invention is shown in FIG. 4. In this embodiment, the electrode head 15 has a shape permitting introduction using an introductory catheter 16. The introductory catheter 16 is sufficiently stiff to maintain the electrode head 15 compressed during implantation. When the electrode head 15 has been advanced to a desired position in a blood vessel 8, the introductory catheter 16 is withdrawn, permitting the electrode head 15 to radially expand to the configuration shown in FIG. 5 and, in the expanded position, to assume the contours (define the surface) of a hollow cylinder. As can be seen in FIG. 5, the cylinder formed by the electrode head 15 consists of at least one filamentous conductor 17 which proceeds in a zig-zag path along the longitudinal axis of the cylinder of the electrode head 15. Only a few zig-zag segments are shown on the surface of the cylinder, so as to clarify the structure of the cylinder formed by the electrode head 15. The cylinder of the electrode head 15 can be provided with a larger number of such zig-zag segments extending between the dashed lines 18 and 19. The electrode cable 1 is connected to the cylinder formed by the electrode head 15 by conductors 20 and 21 at two points, so as to achieve good distribution of current within the cylinder formed by the electrode head 15.

Figure 6:
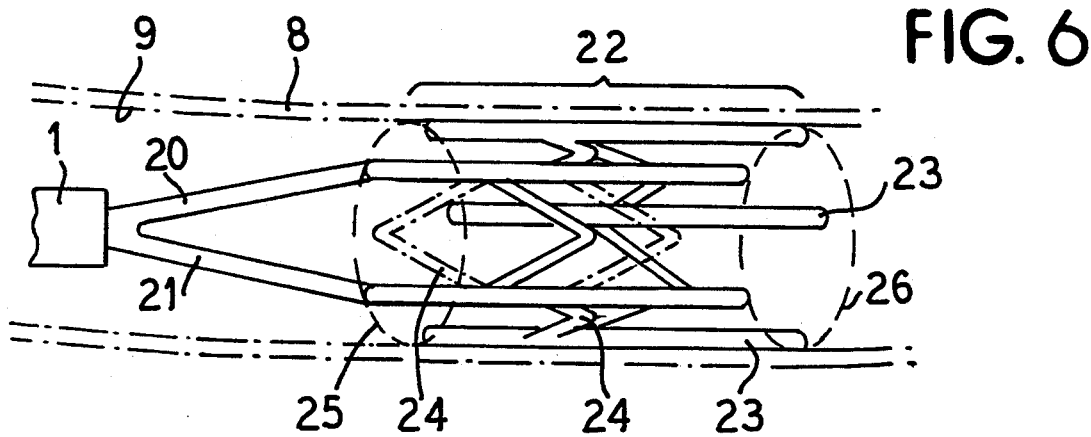

Another example of an electrode head constructed in accordance with the principles of the present invention which is introducible using an introductory catheter is shown in FIG. 6. The electrode head 22 in the embodiment of FIG. 6 is formed by parallel, filamentous conductors 23 which, in an expanded position, extend along the longitudinal axis of a cylinder formed by the electrode head 22, and which are interconnected by compressible connector bodies 24. In the example shown in FIG. 6, the connector bodies 24 are formed by a plurality of outwardly projecting and inwardly projecting V-shaped bodies, which can be made of conductive material so as to increase the defibrillation area of the cylinder formed by the electrode head 22. The tip of the V formed by each of the connector bodies 24 extends parallel to the longitudinal axis of the electrode device. The cylinder formed by the electrode 22 can be provided with a large number of such filamentous conductors 23, extending between the dashed lines designating the contours of the ends of imaginary cylindrical surface of the cylinder formed by the electrode head 22.

Figure 7:
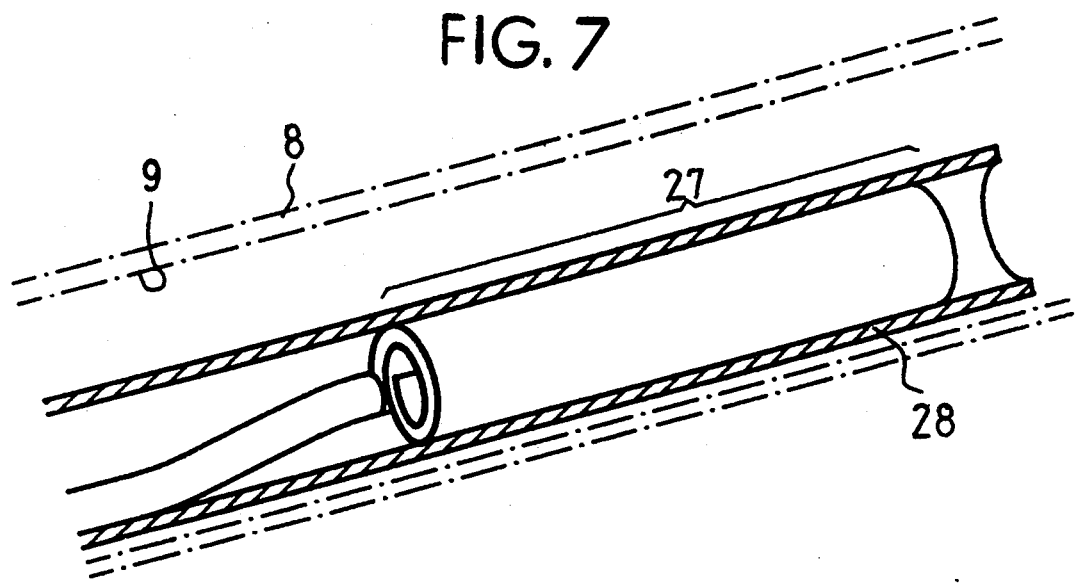

In the embodiment of FIG. 7, an electrode head 27 is shown which is formed by at foil which, in an unexpanded position, is helically rolled and is maintained compressed by an introductory catheter 28. When the introductory catheter 28 is withdrawn, the electrode head 27 expands by unrolling into a cylinder having a surface which presses against the surrounding vascular wall 9, thereby achieving pressure affixing of the cylinder formed by the electrode head 27. The defibrillation area of the cylinder formed by the electrode head 27 is very large.

The above-described electrode heads 5, 10, 15, 22 and 27 and the cylinders respectively formed thereby, can consist of shape-memory metal. This means that the electrode heads can be given a shape, at a first temperature, suitable for implantation, and will then subsequently assume the described cylindrical shape at a second temperature, preferably at body temperature. In such instances, implantation aids such as stylets and introductory catheters, are unnecessary. The conductors constituting the cylinder in the different examples, and the foil in the embodiment of FIG. 7, can be provided with a layer of insulation on the side which presses against the surrounding vascular wall, so as to prevent any damage to the vascular wall by burning during defibrillation. If such a layer of insulation is provided, the entire interior of the cylinder constitutes the defibrillation surface.

Figure 8:
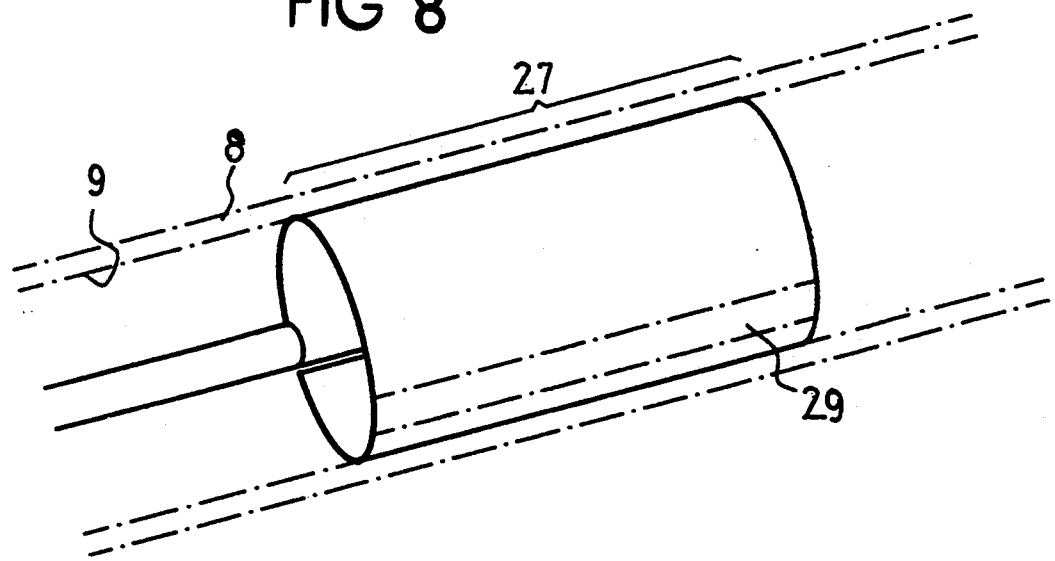

The exterior of the cylinder formed by the various electrode heads can alternatively be provided with a defibrillation surface which extends along the longitudinal axis of the cylinder. An example of such a defibrillation surface 29 is indicated by dot-dashed lines in FIG. 8. In the other embodiments, such a surface may be formed by an uninsulated wire or an uninsulated zig-zag segment, the rest of the cylinder being insulated. In this manner, the implanting physician can aim the current field in the desired direction by rotating the cylinder around its longitudinal axis during implantation, thereby achieving an advantageous distribution of current within the heart tissue.

The electrode head can be provided with different configurations, other that the ones illustrated herein, without departing from the inventive concept. A common feature of the electrode heads of all of the embodiments is that they are radially expandable and that the form, in the expanded position, at least the contours of a hollow body.

Although modifications and changes may be suggested by those skilled in the art, it is the intention of the inventors to embody within the patent warranted hereon all changes and modifications as reasonably and properly come within the scope of their contribution to the art.

We claim as our invention:

1. A defibrillation electrode for intravascular siting in a patient comprising:
   a flexible electrode cable containing at least one elongate, electrically insulated conductor having an electrode head formed by a helically wound continuation of said elongate conductor and insulating an uninsulated conductor portion, said electrode head having at least one defibrillation surface for delivering defibrillation pulses to the heart; and
   said electrode head being radially expandable from a non-expanded state to an expanded state, and defining in the expanded state the contours of a hollow body formed by electrically insulated windings of said helically wound continuation with said uninsulated conduction portion extending straight between said windings.

2. A defibrillation electrode as claimed in claim 1 wherein said hollow body has an outer diameter exceeding a diameter of a blood vessel in which said defibrillation electrode is to be sited for affixing said hollow body to a surrounding vascular wall after introduction into said blood vessel.

3. A defibrillation electrode as claimed in claim 1 wherein said hollow body is expandable along a longitudinal axis thereof.

4. A defibrillation electrode as claimed in claim 1 wherein said elongate conductor comprises a helically wound conductor, and wherein said elongate conductor and said electrode head have a continuous channel therein extending along the entire length of the defibrillation electrode, adapted to receive a stylet.

5. A defibrillation electrode as claimed in claim 1 wherein said hollow body has the shape of a cylinder.

6. A defibrillation electrode as claimed in claim 1 further comprising an introductory catheter adapted to receive said electrode head in said unexpanded state.

7. A defibrillation electrode as claimed in claim 1 wherein said electrode head consists of shape-memory metal.

8. A defibrillation electrode as claimed in claim 1 wherein said hollow body has an interior surface and an exterior surface, and further comprising an insulating layer covering said exterior surface of said hollow body so that said interior surface forms a defibrillation surface.

9. A defibrillation electrode as claimed in claim 1 wherein said hollow body has a longitudinal axis, and wherein said hollow body has a defibrillation surface extending along said longitudinal axis.

10. A defibrillation electrode for intravascular siting in a patient comprising:
    a flexible electrode cable containing at least one elongate, electrically insulated conductor having an electrode head formed by a plurality of parallel, filamentous conductors forming a cylinder and extending along a longitudinal axis of said cylinder, and a plurality of compressible connector bodies interconnecting said filamentous conductors, said electrode head having at least one defibrillation surface for delivering defibrillation pulses to the heart; and said electrode head being radially expandable from a non-expanded state to an expanded state, and defining in the expanded state the contours of a hollow body.

11. A defibrillation electrode as claimed in claim 10 wherein said connector bodies consist of a plurality of outwardly projecting and inwardly projecting V-shaped bodies.

12. A defibrillation electrode as claimed in claim 11 wherein said connector bodies consist of electrically conducting material.

13. A defibrillation electrode as claimed in claim 10 wherein said hollow body has an outer diameter exceeding a diameter of a blood vessel in which said defibrillation electrode is to be sited for affixing said hollow body to a surrounding vascular wall after introduction into said blood vessel.

14. A defibrillation electrode as claimed in claim 10 wherein said hollow body is expandable along a longitudinal axis thereof.

15. A defibrillation electrode as claimed in claim 10 wherein said elongate conductor comprises a helically wound conductor, and wherein said elongate conductor and said electrode head have a continuous channel therein extending along the entire length of the defibrillation electrode, adapted to receive a stylet.

16. A defibrillation electrode as claimed in claim 10 further comprising an introductory catheter adapted to receive said, electrode head in said unexpanded state.

17. A defibrillation electrode as claimed in claim 10 wherein said electrode head consists of shape-memory metal.

18. A defibrillation electrode as claimed in claim 10 wherein said hollow body has an interior surface and an exterior surface, and further comprising an insulating layer covering said exterior surface of said hollow body so that said interior surface forms a defibrillation surface.

19. A defibrillation electrode as claimed in claim 10 wherein said hollow body has a longitudinal axis, and wherein said hollow body has a defibrillation surface extending along said longitudinal axis.

* * * * *